United States Patent [19]

Cragoe, Jr.

[11] Patent Number: 4,782,073

[45] Date of Patent: Nov. 1, 1988

[54] AMIDES OF [(5,6-DICHLORO-3-OXO-9-ALPHA-SUBSTITUTED-2,3,9,9-ALPHA-TETRAHYDROFLUOREN-7-YL-OXYL]ACETIC ACIDS, AND PHARMACEUTICAL COMPOSITIONS THEREOF

[75] Inventor: Edward J. Cragoe, Jr., Lansdale, Pa.

[73] Assignee: Merck & Co., Inc., Rahway, N.J.

[21] Appl. No.: 946,544

[22] Filed: Dec. 24, 1986

[51] Int. Cl.$^4$ ............... C07D 257/06; C07D 143/72; C07D 125/08; A61K 31/41

[52] U.S. Cl. ................................ 514/381; 514/605; 514/609; 548/251; 558/300; 564/99

[58] Field of Search ............... 548/251; 514/381, 605, 514/609; 564/99; 558/300

[56] References Cited

U.S. PATENT DOCUMENTS

| | | | |
|---|---|---|---|
| 4,316,043 | 2/1982 | Cragoe et al. | 560/53 |
| 4,317,922 | 3/1982 | Cragoe et al. | 562/461 |
| 4,337,354 | 6/1982 | Cragoe et al. | 562/461 |
| 4,356,313 | 10/1982 | Cragoe et al. | 560/53 |
| 4,356,314 | 10/1982 | Cragoe et al. | 560/53 |
| 4,389,417 | 6/1983 | Bourke et al. | 424/317 |
| 4,394,385 | 7/1983 | Cragoe et al. | 424/285 |
| 4,463,208 | 7/1983 | Cragoe et al. | 562/462 |
| 4,465,850 | 8/1984 | Cragoe et al. | 560/53 |
| 4,579,869 | 4/1986 | Cragoe et al. | 514/561 |
| 4,604,396 | 8/1986 | Cragoe et al. | 514/256 |

OTHER PUBLICATIONS

J. Med. Chem. (1982) Cragoe, et al. 25, pp. 567–679.
J. Med. Chem. (1986) Cragoe, et al. 29, pp. 825–842.

*Primary Examiner*—Glennon H. Hollrah
*Assistant Examiner*—D. B. Springer
*Attorney, Agent, or Firm*—Charles M. Caruso; Hesna J. Pfeiffer

[57] ABSTRACT

The invention relates to novel amides of [(5,6-dichloro-3-oxo-9a-substituted-2,3,9,9a-tetrahydrofluoren-7-yl)oxy]acetic acids, their derivatives, and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, the neurological problems caused by AIDS, cerebral hemorrhage, cerebral tumors, encephalomyelitis, spinal cord injury, hydroephalus, post-operative brain injury trauma, edema due to cerebral infections, various brain concussions and elevated intracranial pressure.

7 Claims, No Drawings

AMIDES OF [(5,6-DICHLORO-3-OXO-9-ALPHA-SUBSTITUTED-2,3,9,9-ALPHA-TETRAHYDROFLUOREN-7-YL-OXYL]ACETIC ACIDS, AND PHARMACEUTICAL COMPOSITIONS THEREOF

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, the neurological problems caused by AIDS, cerebral hemorrhage, encephalomyelitis, hydrocephalus, post-operative brain injury, cerebral infections, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Two recent publications, one entitled "*Agents for the Treatment of Brain Injury*" 1. (Aryloxy)alkanoic Acids, by Cragoe et al, J. Med. Chem., (1982) 25, 567–579 and the other, "Agents for the Treatment of Brain Edema" and 2. [2,3,9,9a-tetrahydro-3-oxo-9a-substituted-1H-fluoren-7-yl)oxy]acetic Acids and their Analogs", by Cragoe et al., Med. Chem., 29, 825–841 (1986), report recent experimental testing of agents for treatment of brain injury and review the current status of treatment of brain injury. Additionally, U.S. Pat. No. 4,316,043, 4,317,922, 4,337,354, 4,356,313, 4,356,314, 4,389,417, 4,394,385, 4,463,208, 4,465,850, 4,579,869, and 4,604,396 disclose certain alkanoic acids, cycloalkanoic acids or their amidine analogs for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

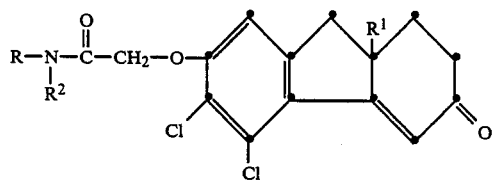

wherein:
R is $-CN$, $-SO_2-C_1-C_6$-alkyl,

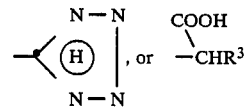

(derived from natural chiral amino acids); $R_1$ is lower alkyl, branched or unbranched, containing from 1 to 3 carbon atoms such as methyl, ethyl, n-propyl and isopropyl and hydroxy-loweralkyl, containing 1 to 3 carbon atoms as 2-hydroxyethyl;

$R^2$ is H, and $R^2$ and $R^3$ may be joined to form a ring; $R^3$ is the alpha substituent of a natural chiral amino acid, thus it may be $CH_3$, $(CH_3)_2CH$, $(CH_3)_2CHCH_2C_2H_5(CH_3)CH-$, $HOCH_2CH_2-$, $CH_3CH(OH)-$, $C_6H_5CH_2-$, $4-(HO)C_6H_4CH_2-$, $HSCH_2-$, $HOOCCH(NH_2)CH_2SSCH_2-$, $CH_3SCH_2CH_2-$, $HOOCCH_2-$, $H_2NCOCH_2-$, $HOOCCH_2CH_2-$, $H_2NCOCH_2CH_2-$, $HN-C(=NH)NH(CH_2)_3-$, $NH_2(CH_2)_4$, $H_2NCH_2CH(CH)(CH_2)_2-$, $H_2N(CH_2)_3$,

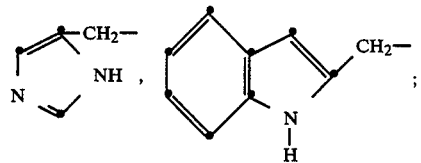

Thus $R^3$ may be derived from alanine, valine, leucine, isoleucine, serine, threonine, phenylalanine, tyrosine, cysteine, methionine, aspartic acid, asparagine, glutamic and glutamine, arginine, lysine, hydroxylysine, ornithine, histidine and tryptophane, respectively; when R and $R^2$ are joined to form a ring the $R+R^2$ may be $-(CH_2)_3-$or $-CH_2CH(OH)CH_2-$; Thus being derived from proline or hydroxyproline, respectively.

Since the 9α-carbon $R^1$ atom and the carbon atom to which $R^3$ is attached are asymmetric, the compounds of the invention can be racemic or diasteriomeric. However, these compounds or their precursors can be resolved so that the pure enantiomers can be prepared, thus the invention includes the pure enantiomers. Since $R^3$ or ($R^2$ and $R^3$) are always derived from natural (L) amino acids, the number of isomers is reduced. An important point is that since some of the racemates consist of one.

Since the 9a-carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates possess of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate It should be noted that, since certain of the novel amides of this invention are derived natural amino acids that these compounds may have the advantage of benefitting from the specific amino acid transport systems that allow such compounds to be transported into the brian and thus achieve high drug levels in the brain Likewise, since the products of the invention are acidic, the invention also includes the obvious pharmaceutically acceptable salts such as the sodium, potassium, ammonium, trimethylammonium, piperazinium, 1-methylpiperazinium, guanidinium, bis-(2-hydroxyethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel amides of [(5,6-dichloro-3-oxo-9a-substituted-2,3,9,9a-tetrahydrofluoren-7-yl)oxy]acetic acids and their salts, it also includes their derivatives, such as oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

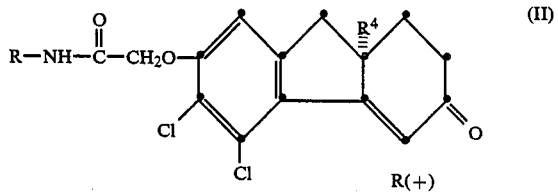

(II)

wherein:
R is as defined above;
R$^4$ is lower alkyl, branched or unbranched, or hydroxy-lower alkyl, each containing from 1 to 3 carbon atoms.

Also included are the enantiomers of each racemate.

A preferred compound is R(+)-N-ethansulfonyl[5,6-dichloro-3-oxo-9a-propyl-2,3,9,9a-tetrahydro-1H-fluoren-7-yl)oxy]acetamide.

Also preferred is R(+)-N-methanesulfonyl[(5,6-dichloro-3-oxo-9a-propyl-2,3,9,9a-tetrahydro-1H-fluoren-7-yl)oxy]acetamide.

Also preferred is R(+)-N-cyano-[(5,6dichloro-3-oxo-9a-propyl-2,3,9,9a-tetrahydro-1H-fluoren-7-yl)oxy]acetamide.

Also preferred is R(+)-N-(5-tetrazolyl)-[(5,6-dichloro-3-oxo-9a-propyl-2,3,9,9a-tetrahydro-1H-fluoren-7-yl)oxy]acetamide.

Also preferred is {R(+)-N-[(5,6-dichloro-3-oxo-9a-propyl-2,3,9,9a-tetrahydro-1H-fluoren-7-yl)oxy]acetyl}-S(+)-serine.

Also preferred is {[R(+)-N-[(5,6-dichloro-3-oxo-9a-propyl-2,3,9,9a-tetrahydro-1H-fluoren-7-yl)oxy]acetyl}-S(+)-leucine.

Also preferred is {R(+)-N-[(5,6-dichloro-3-oxo-9a-propyl-2,3,9,9a-tetrahydro-1H-fluoren-7-yl)oxy]acetyl}-S(−)-phenylalanine.

Also preferred is {R(+)-N-[(5,6-dichloro-3-oxo-9a-propyl-2,3,9,9a-tetrahydro-1H-fluoren-7-yl) oxy]acetyl}-S,(-)-tyrosine.

Also preferred is {R(+)-N-[(5,6-dichloro-3-oxo-9a-propyl-2,3,9,9a-tetrahydro-1H-fluoren-7-yl)oxy]acetyl}-S(−)-histidine.

Also preferred is {R(+)-N-{[5,6-dichloro9a-(hydroxyethyl)-3-oxo-2,3,9,9a-tetrahydro-1H-fluoren-7-yl]oxy}acetyl}-S(−)-proline.

Especially preferred are the pure enantiomers since, in most instances, one enantiomer is more active biologically then its antipode.

Included within the scope of this invention are the pharmaceutically acceptable salts of the novel amides of [(5,6-dichloro-3-oxo-9a-substituted-2,3,9,9a-tetrahydro-1H-fluoren-7-yl)oxy]acetic acids since a major medical use of these compounds is solutions of their soluble salts which can be administered parenterally.

Thus, the acid addition salts can be prepared by the reaction of the amides of [(5,6-dichloro-3-oxo-9a-substituted-2,3,9,9a-tetrahydro-1H-fluoren-7yl)oxy]acetic acids of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl) amine, N-methylglucosamine and the like salts.

The compounds of this invention are unique derivatives of [(5,6-dichloro-3-oxo-9a-substituted-2,3,9,9a-tetrahydrofluoren-7-yl)oxy]acetic acid (III), designed to possess enhanced therapeutic properties. These enhanced effects are obtained by virtue of their unique physical and chemical properties which allow them to be more effectively transported to their site of action.

It will be noted that the compounds possess acidic character which allows for the formation of salts derived from organic or inorganic bases hhich possess sufficient water solubility to permit the compounds to be administered in aqueous milieu by a parenteral route.

The compounds are synthesized by reacting a [(5,6-dichloro-3-oxo-9a-substituted-2,3,9,9a-tetrahydrofluoren-7-yl)oxy]acetic acid (III) with 1,1'carbonyldiimidazole(IV) to form V. The reaction is conducted in an inert solvent, such as tetrahydrofuran and the like. The reaction of these with an amine such as RNH$_2$ (VI) gives the corresponding amide I, which may constitute the desired product where R is

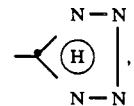,

—SO$_2$CH$_3$, —SO$_2$C$_2$H$_5$, —CN, etc. However, if R is derived from an amino acid, then it is convenient to conduct the reaction with an amino acid ester (VIIa or VIIb,) which upon reaction with V gives the ester (VIIIa or VIIIb,). If the ester exists as a hydrochloride or dehydrochloride salt, one or two molar equivalents of triethylamine is added to produce the free base. Treatment of VIIIa or VIIIb with an aqueous alcoholic base, such as sodium hydroxide or potassium hydroxide with heating and stirring followed by acidification gives the amino acid derivative Ia or Ib.

VIIa and VIIb are esters of natural amino acids (and that is a major intention of this invention), they will be

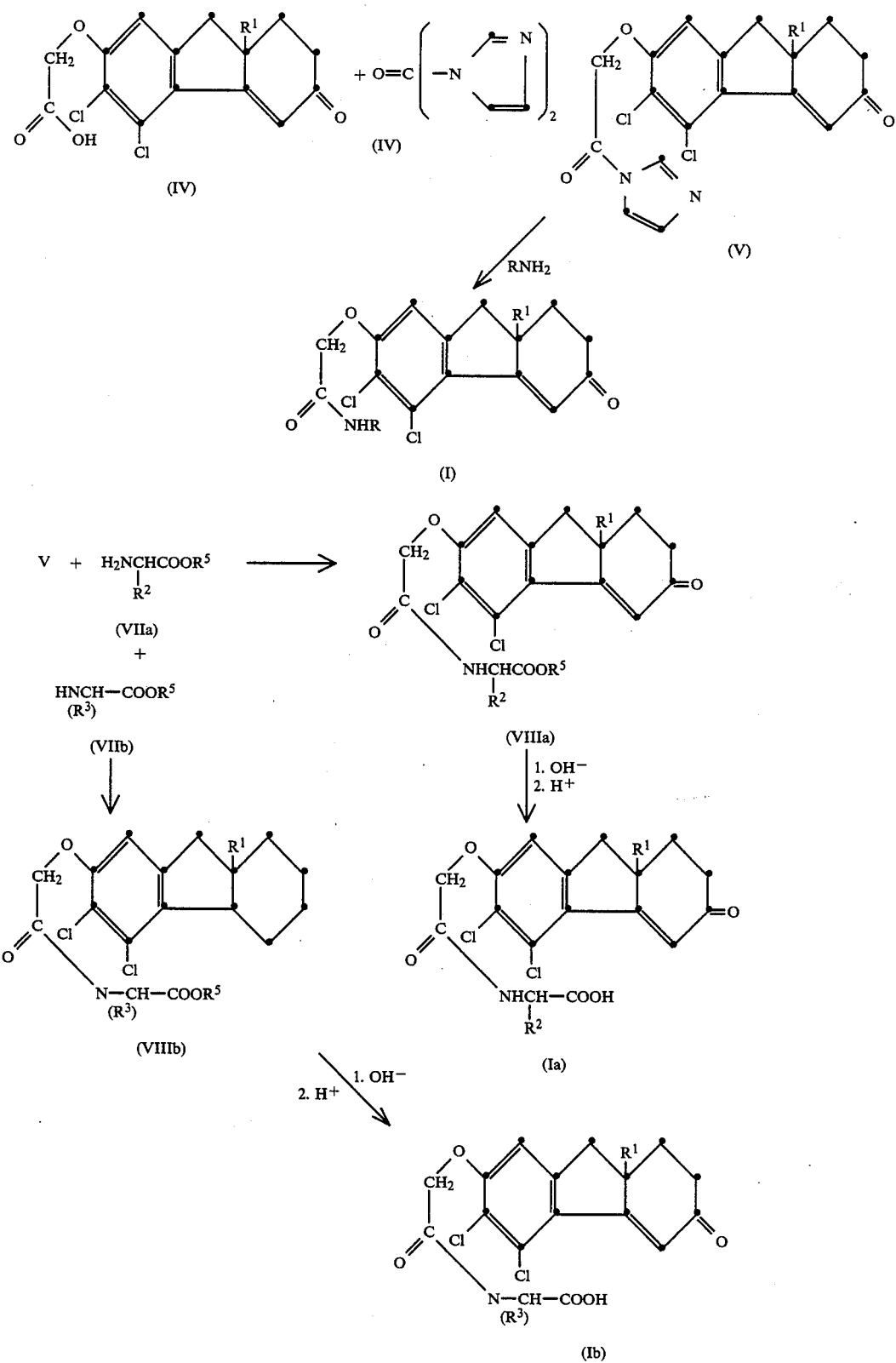

It is to be noted that the compound if Formula III is a single enantiomer i.e., (R+), V and I are a single enantiomer. Furthermore, if the compound of Formula VIIa and VIIb are esters of natural amino acids pure enantiomers (the L form) and their products (Ia and Ib) will possess a second chiral center in their molecules.

It is to be recognized that these compounds of Formula I possess an asymmetric carbon atom at position 9a and, therefore, consist of racemates composed of two enantiomers. The resolution of the two enantiomers may be accomplished by forming a salt of the racemic mixture with an optically active base such as (+) or (−) amphetamine, (−) cinchonidine, dehydroabietylamine, (+) or (−)-α-methylbenzylamine, (+) or (−)-α-(1-naphthyl)ethylamine, (+) cinchonine, brucine. or strychnine and the like in a suitable solvent such as methanol, ethanol, 2-propanol, benzene, acetonitrile, nitromethane, acetone and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

Alternatively, the precusor acids (III) can be conveniently resolved before reaction with IV and therefore, the intermediates (VIIIa and VIIIb) and the final products (I, Ia and Ib) will be pure enantiomers.

Since the products of Formulas Ia and Ib the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxyethyl)ammonium, N-methylglucosammonium and the like salts.

These salts are preferably formed by the reaction of the appropriate base with the compound of Formula I or II.

The reaction may be conducted in water but it is preferred to conduct the reaction in an organic solvent, such as ether, ethanol, N,N-dimethylformamide and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, the neurological problems caused by AIDS, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous adminiand stration of drugs of the type of Formula I in the form of their salts is superior.

A recommended dosage range for treatment is expected to be from 0.05 mg/kg to 15 mg/kg of body weight as a single dose, preferably from 0.5 mg/kg to 10 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 4, 8 and 10 mg/kg of body weight can be given at 6 hour intervals. If necessary, 4 additional doses of 10 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an anti-inflammatory steroid. These steroids are of some, albeit limited, use in control of white matter edema associated with is chemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable oarboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29–31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R. ; Kimelberg, H, K,. Eds.; Raven Press: New York, 1979; p 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V. ; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO^-_3$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO^-_3$ to incubation media stimulates statisticaly significant and comparable increases in cerebrocortical tissue swelling and ion levels. After addition of drug to the incubation media, detailed drug concentration-response curves are then obtained. The data are expressed as percent $HCO^-_3$-stimulated swelling vs. drug concentration, from which the concentration of drug providing 50% inhibition of $HCO^-_3$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims.

All temperatures in the examples are in Centigrade unless otherwise indicated.

That the compounds of this invention have intrinsic activity in preventing edema of the relevant portions of the brain are revealed by their activity in the in vitro cat cerebrocortical assay. The assay is conducted as follows:

Adult cats of 2–3 kg body weight were employed in tissue slice studies. Prior to sacrifice by cervical crush and brain sampling[1], the animals were anesthetized with ketamine hydrochloride (Ketaset), 10 mg/kg im. Eight (three control, five experimental) pial surface cerebrocortical tissue slices (0.5-mm thick; approximately 150 mg initial fresh weight) were cut successively with a calibrated Stadie-Riggs fresh tissue microtome without moistening and weighed successively on a torsion balance. During the slice preparation, all operations except weighing were confined to a humid chamber. Each slice was rapidly placed in an individual Warburg flask containing 2 mL of incubation medium at room temperature. The basic composition of the incubation media, in millimoles per liter was as follows: glucose, 10; $CaCl_2$, 1.3; $MgSO_4$, 1.2; $KH_2SO_4$, 1.2; HEPES (N-2-hydroxyethylpiperazine-N'-2-ethanesulfonic acid, titrated with NaOH to pH 7.4), 20. Except when adding $HCO^-_3$, the osmolarity of the media was maintained isosmotic (approximately 285 mOsm/L) by reciprocal changes of $Na^+$ or $K^+$ to achieve a concentration of $K^+$ of 27 mM. The basic medium was bubbled for 30 minutes with 100% $O_2$ before use. When added, $NaHCO_3$ or triethylammonium bicarbonate (TEAB) was initially present in the sidearm of each flask at an initial concentration of 50 mM in 0.5 mL of complete medium. Nonbicarbonate control slices were incubated at 37° C. in 2.5 mL of basic medium for 60 minutes. Bicarbonate control slices were similarly incubated for an initial 20 minutes at 37° C. in 2.0 mL of basic medium to which was added from the sidearm an additional 0.5 mL of incubation medium containing 50 mM $HCO^-_3$, which, after mixing, resulted in a $HCO^-_3$ concentration of 10 mM and a total volume of 2.5 mL. The incubation continued for an additional 40 minutes. The various compounds tested (Table I) were dissolved by forming the sodium salts by treatment with a molar equivalent of $NaHCO_3$ and diluting to the appropriate concentrations. Just prior to incubation, all flasks containing $HCO^-_3$ were gassed for 5 minutes with 2.5% $CO_2$/97.5% $O_2$ instead of 100% $O_2$.

Following the 60 minute incubation period, tissue slices were separated from incubation medium by filtration, reweighed, and homogenized in 1 N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration was measured by the amount of $HCO^-_3$ stimulated swelling that occurred in its presence, computed as a percent of the maximum possible (legend, Table II). Tissue and media $Na^+$ and $K^+$ were determined by emission flame photometry with $Li^+$ internal standard; $Cl^-$ was determined by amperometric titration. Tissue viability during incubation was monitored by manometry. A full discussion of methods is to be found elsewhere. [2] [2]Bourke, R. S.; Tower, D. B. *J. Neurochem.* 1966 13, 1071.

These compounds are typical of those of the invention.

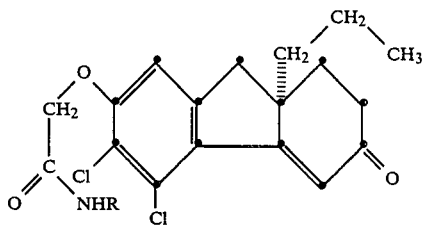

| R | $I_{50}$ (M)[a] |
|---|---|
| $-SO_2CH_3$ | $2 \times 10^{-8}$ |
| $-SO_2C_2H_5$ | $10^{-8}$ |
| $-CH(CH_3)COOH$ | $8 \times 10^{-11}$ | a. Concentration giving 50% inhibition of swelling

That these compounds exhibit the desirable physical and chemical properties sought is seen in the following table:

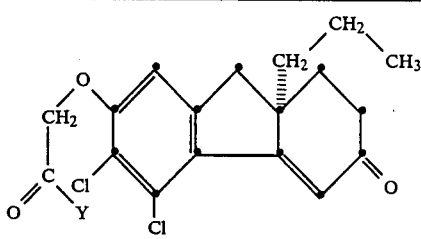

| Y | pV-a | Distribution in Octanol/ 7.4 Buffer | Protein Binding |
|---|---|---|---|
| $NHSO_2CH_3$ | 4.25 | 94.2 | 97.2 |
| $NHSO_2C_2H_5$ | 4.10 | 97 | — |
| NHCN | 3.65 | 98.3 | 98.4 |
| $NH-CH(COOH)-CH(CH_3)_2$ | 4.60 | 98.9 | 97 |
| $NH-CH(COOH)-CH_2C_6H_5$ | 4.58 | 99.3 | 94.3 |
| $NH-CH(COOH)-CH_2-C_6H_4-4-OH$ | 4.12 | 97 | 97.8 |
| $NH-CH(COOH)-CH_2OH$ | 4.10 | 81 | 97.6 |
| $NH-CH(COOH)-CH_2-\text{(imidazole)}$ | 6.9 | 89.8 | 92.1 |

-continued

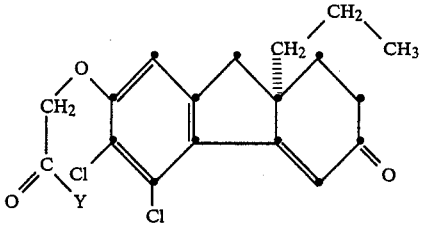

| Y | pV-a | Distribution in Octanol/ 7.4 Buffer | Protein Binding |
|---|---|---|---|
| NH—⟨N=N / N—N−H⟩ | 3.78 | 92 | 98.1 | a. Distribution between octanol and aqueous buffer at pH = 7.4 were determined as described by R. A. Sherrer and S. M. Howard, J. Med. Chem. (1977) 20, 53.
b. % Bound using $4 \times 10^{-4}$ M bovine serum albumin.

EXAMPLE 1

In Vitro Cerebrocortical Tissue Slice Assay

Adult cats of 2–3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 mL of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxyethyliperazine-N'-2-ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 mL of complete medium. Nonbicarbonate control slices are incubated at 37° C. in 2.5 mL of basic medium for 60 minutes. Bicarbonate control slices are similarly incubated for an initial 20 minutes at 37° C. in 2.0 mL of basic medium to which is added from the sidearm an additional 0.5 mL of incubation medium containing 50 mM $HCO^-_3$, which, after mixing, results in a $HCO^-_3$ concentration of 10 mM and a total volume of 2.5 mL. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2/97.5\%$ $O_2$ instead of 100%

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO^-_3$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

N-Ethanesulfonyl-[5,6-dichloro-3-oxo-9a-propyl-2,3,9,9a-tetrahydro-1H-fluoren-7-yl)oxy]acetamide

[(5,6-Dichloro-3-oxo-9a-propyl-2,3,9,9a-tetrahydro-1H-fluoren-7-yl)oxy]acetic acid (2.21g., 6 mMole) and 1,1'-carbonyldiimidazole (1.07 g., 6.6 mMole) were united in sieve-dried tetrahydrofuran (75 mL) in an atmosphere of dry nitrogen. The mixture was stirred at ambient temperature for 30 minutes to form the 1-acylimidazole. Then, ethanesulfonamide (880 mg, 8.06 mMole) was added and stirring at ambient temperature was continued for 30 hours, followed by heating at reflux for 48 hours.

The solvent was removed by evaporation in vacuo and the residue dissolved in water and acidified with hydrocholic acid The precipitate that formed was removed by filtration, suspended in water basified with sodium bicarbonate and filtered to remove the insoluble material. The filtrate was acidified with hydrochloric acid and to precipitate removed by filtration, washed with water and dried. The dry solid (2.4 g.) was dissolved in a little tetrahydrofuran and placed on a column chromatograph of silica gel (300 g.) and eluted with a mixture of methylene chloride/tetrahydrofuran acetic acid 50/1/1 (v.v.v.). Selecting the appropriate cuts with an R. F. of 0.56 using the same system in thin layer chromatography, the solvent was removed in vacuo to give 2.3 g. of residue. The residue was treated with isopropyl alcohol (10 mL) and the white solid that separated was removed by filteration, washed with isoproyl alcohol (1 mL) and dried. The yield of product was 1.39 g., m.p. 158.5°–159.5° C. Recrystallization from ethanol (15 mL) gave 1.30 g. of product, m.p. 160.5°–161.5° C.

Anal. Calc. for $C_{20}H_{23}Cl_2NO_5S$: C, 52.18; H, 5.04; N, 3.04%. Found: C, 51.89; H, 4.99; N, 2.89%.

EXAMPLE 3

R(+)-Ethanesulfonyl-[(5,6-dichloro-3-oxo-9a-propyl-2,3,9,9a-tetrahydro-1H-fluoren-7-yl)oxy]acetamide By carrying out the reaction as described in Example 2, except that the racemic [(5,6-dichloro-3-oxo-9a-propyl-2,3,9,9a-tetrahydro-1H-fluoren-7-yl)oxy]acetic acid is replaced by an equal amount of R(+)-[(5,6-dichloro-3-oxo-9a-propyl-2,3,9,9a-tetrahydro-1H-fluoren-7-yl)oxy]acetic acid. There is obtained R(+)-Ethanesulfonyl-[(5,6-dichloro-3-oxo-9a-propyl-2,3,9,9a-tetrahydro-1H-fluoren-7-yl)oxy]acetamide.

EXAMPLE 4

R(+)-N-Methylsulfonyl-[(5,6-dichloro-3-oxo-9a-propyl-2,3,9,9a-tetrahydro-1H-fluoren-7-yl)oxy]acetamide.

The synthesis of this compound is achieved by the procedure described in Example 1 except that the racemic [(5,6-dichloro-3-oxo-9a-propyl-2,3,9,9a-tetrahydro-1H-fluoren-7-yl)oxy]acetic acid is replaced by an equal amount of the R(+) enantiomer and the ethanesulfonamide is replaced by an equimolar amount of methanesulfonamide. Thus, there is obtained 440 mg of product, m.p. 194.5°–195.5° C.

Anal. Calc. for $C_{19}H_{21}Cl_2NO_5S$: C, 51.12; H, 4.74; N, 3.14. Found: C. 51.09; H, 4.70; N, 307.

EXAMPLE 5

R(+)-N-Cyano-[(5,6-dichloro-3-oxo-9a-propyl-2,3,9,9a-tetrahydro-1H-fluoren-77-yl)oxy]acetamide R(+)-[(5,6-Dichloro-3-oxo-9a-propyl-2,3,9,9a-tetrahydro-1H-fluoren-7-yl)oxy]acetic acid (2.95 g., 8 mMole) and 1,1'-carbonyldiimidazole (1.46 g., 9 mMole) in sieve-dried tetrahydrofuran (80 m.p.) were stirred at ambient temperature for 25 minutes in an atmosphere of dry nitrogen. Cyanamide (71 mg 17 mMole) was added and stirring continued for 62 hours at ambient temperature. The solvent was removed by evaporation in vacuo and the residue treated with water and filtered. The filtrate was added to water containing hydrochloric acid. The precipitate that formed was removed by filtration, treated with water containing sodium biocarbonate and filtered. The filtrate was poured into water containing hydrochloric acid and the precipitate that formed removed by filtration washed with water and dried. The yield was 3.35 g. The product was dissolved in tetrahydrofuran and placed on 10 (335 mg per plate) American Scientific Products 7¾ inch square plates (20×20 cm.) containing silica gel 60F-254 precoated to a thickness of 2.0 mm. The plates were developed with methylene chloride/tetrahydrofuran/acetic acid 50/5/2 (v.v.v.). The product which appeared at the 5 to 45 mm level (the impurities were higher) were removed, pulverized and extracted with 20% acetic acid in tetrahydrofuran. The solvents were removed by evaporation in vacuo and the residue treated with water containing sodium bicarbonate, filtered and the filtrate acidified with hydrochloric acid. The precipitate that formed was removed by filtration, washed with water and dried. The product (2 g.) was dissolved in methylene chloride (25 mL) but on standing crystallized. Te solid was removed by filtration and dried. The yield of product was 1.32 g.

Anal. Calc. for $C_{19}H_{18}Cl_2N_2O_3 \cdot \frac{1}{2}H_2O$: C, 56.72; H, 4.76; N, 6.96; Cl, 17.63. Found: C, 56.81; H, 4.55, N, 6.73; Cl, 17.81.

EXAMPLE 6

R(+)-N-(5-Tetrazolyl)-[5,6-dichloro-3-oxo-9a-propyl-2,3,9,9a-tetrahydro-1H-fluoren-7-yl)oxy]acetamide R(+)[(5,6-Dichloro-3-oxo-9a-propyl-2,3,9,9a-tetrahydro-1H-fluoren-7-yl)oxy]acetic acid (3.69 g., 10 mMole) and 1,1'-carbonyldiimidazole (1.95 g., 12 mMole) in dry tetrahydrofuran (125 mL) was stirred at ambient temperature in an atmosphere of dry nitrogen for 30 minutes. Then, 5-aminotetrazole (1.24 g., 12 mMole) in 1-methyl-2-pyrrolidinone (3.6 mL total volume) was added and the mixture was stirred for 24 hours. The solvents were evaporated at reduced pressure and the residue dissolved in water and rapidly acidified with hydrochloric and to give a zellus precipitate. The solid was removed by filtration, washed with water and dried; yield 4.39 g.

The product was chromatographed on a silica gel (150 gm.) column 40 mm×30 cm using methylene chloride/tetrahydrofuran/acetic acid, 50/5/2 (V.V.V.) for elution. The proper fractions were selected using thin layer chromatography and the solvents removed in vacuo. The residue was treated with boiling acetonitrile, filtered and worked with acetonitrile and dried to give 1.67 g. of product, m.p. 256°–257° C.

Anal. Calc. for $C_{19}H_{19}Cl_2N_5O_3$: C, 52.30; H, 4.39: N, 16.05. Found: C, 52.37; H, 4.51: N, 15.79.

EXAMPLE 7

{R(+)-N-[(5,6-Dichloro-3-oxo-9a-propyl2,3,9,9a-tetrahydro-1H-fluoren-7-yl)oxy]acetyl}S(+)-serine R(+)[(5,6-Dichloro-3-oxo-9a-propyl-2,3,9,9a-tetrahydro-1H-fluoren-7-yl)oxy]acetic acid (3.69 g., 10 mMole) and 1,1'-carbonyldiimidazole (1.95 g., 12 mMole) in dry tetrahydrofuron (100 mL) was stirred in an atmosphere of dry nitrogen at ambient temperatures for 30 minutes. S(+) Serine methyl ester hydrochloride (1.87 g., 12 mMole) and triethylamine (1.21 g., 12 mMole) was added and the mixture stirred at ambient temperature for 16 hours. The solvent was removed by distillation vacuo and the residue dissolved in methylene chloride (75 mL), washed 3 times with water (50 mL portions) and dried over anhydrous magnesium sulfate. The solvent was removed by evaporation in vacuo and the residue treated with ethanol (25 mL) and 0.2 normal sodium hydroxide solution (75 mL). The mixture was stirred and refluxed for 25 minutes, whereby a clear solution formed. The mixture was cooled in ice and acidified with hydrochloric acid. The solid that separated was removed by filteration, treated with water containing sodium bicarbonate, filtered and the filtrate acidified with hydrochloric acid. The precipitate that formed was removed by filtration, washed with water and dried. The yield was 4.31 g. The product was chromatographed over silica gel (150 g.) using a 40 mm×30 cm column and eluted with methylene chloride/tetrahydrofuran/acetic acid 20/5/1 (v.v.v.). The appropriate functions were taken as revealed by thin layer chromatography and the solvents removed by distillation in vacuo. The residue was treated with water containing sodium bicarbonate, filtered and the filtrate acidified with hydrochloric acid. The precipitate that formed was removed by filtration, washed with water and dried. The yield was 2.62 g.

Anal. Calc. for $C_{21}H_{23}Cl_2NO_6$: C, 55.17; H, 5.08; N, 3.07. Found: C, 55.17; H, 5.17; N, 3.24.

EXAMPLE 8

{R(+)-N-[(5,6-Dichloro-3-oxo-9a-propyl-2,3,9,9a-tetrahydro-1H-fluoren-7-yl)oxy]acetyl}S(+)-leucine R(+)[(5,6,-Dichloro-3-oxo-9a-propyl-2,3,9,9a-tetrahydro-1H-fluoren-7-yl)oxy]acetic acid (3.69 g., 10 mMole) and 1,1'-carbonyldiimidazole (1.95 g., 12 mMole) in dry tetrahydrofuran (100 mL) was stirred in an atmosphere of dry nitrogen at ambient temperature for 30 minutes. S(+)-leucine methyl ester hydrochloride (1.78 g., 11 mMole) and triethylamine (1.11 g., 11 mMole) was added and the mixture stirred at ambient temperature for 24 hours. The solvent was removed by distillation in vacuo and the residue dissolved in methylene chloride (150 mL), washed 3 times with water (75 mL portions) and dried over anhydrous magnesium sulfate. The solvent was removed by evaporation in vacuo and the residue treated with ethanol (25 mL) and 0.2 normal sodium hydroxide solution (75 mL). The mixture was stirred and refluxed for 45 minutes, whereby a clear solution formed. The mixture was cooled in ice and acidified with hydrochloric acid. The solid that separated was removed by filtration, treated with water containing 1-methylpiperazine, filtered and the filtrate acidified with hydrochloric acid. The precipitate that formed was removed by filtration, washed with water and dried. The yield was 4.44 g., m.p. 96°–98° C.

Anal. Calc. for $C_{24}H_{29}Cl_2NO_5$: C, 59.75; H, 6.06; N, 2.90. Found: C, 59.80; H, 6.21; N, 3.09.

EXAMPLE 9

{R(+)-N-[(5,6-Dichloro-3-oxo-9a-propyl2,3,9,9a-tetrahydro-1H-fluoren-7-yl)oxy]acetyl}-S(−) phenylalanine R(+)[(5,6,-Dichloro-3-oxo-9a-propyl-2,3,9,9a-tetrahydro-1H-fluoren-7-yl)oxy]acetic acid (3.69 g., 10 mMole) and 1,1'-carbonyldiimidazole (1.78 g., 11 mMole) in dry tetrahydrofuran (100 mL) was stirred in an atmosphere of dry nitrogen at ambient temperature for 30 minutes. S(−)Phenylalanine ethyl ester hydrochloride (2.53 g., 11 mMole) and triethylamine (1.11 g., 11 mMole) was added and the mixture stirred at ambient temperature for 24 hours. The solvent was removed by distillation in vacuo and the residue dissolved in methylene chloride (75 mL), washed 3 times with water (50 mL portions) and dried over anhydrous magnesium sulfate. The solvent was removed by evaporation in vacuo and the residue treated with ethanol (15 mL) and 0.2 normal sodium hydroxide solution (75 mL). The mixture was stirred and refluxed for 25 minutes, whereby a clear solution formed. The mixture was cooled in ice and acidified with hydrochloric acid. The solid that separated was removed by filtration, treated with water containing sodium bicarbonate, filtered and the filtrate audified with hydrochloric acid. The precipitate that formed was removed by filtration, washed with water and dried. The yield was 5.11 g. The product was chromatographed over silica gel (150 g.) using a 40 mm×30 cm column and eluted with methylene chloride/tetrahydrofuran/acetic acid 25/1/1 (v.v.v.). The appropriate fractions were taken a revealed by thin layer chromatography and the solvents removed by distillation in vacuo. The residue was treated with water containing sodium bicarbonate and a little ethanol, filtered and the filtrate acidified with hydrochloric acid. The precipitate that formed was removed by filtration, washed with water and dried. The yield was 3.53 g. The solid was treated with water containing a little 1-methylpiperazine, filtered, and the filtrate treated with a little acetic acid then with hydrochloric acid. The precipitate that formed was removed by filtration washed with water and dried. The sample was dissolved and precipitated again as described above. the final yield of product was 2.95 g.

Anal. Calc. for $C_{27}H_{27}Cl_2NO_5$: C, 62.79; H, 5.27; N, 2.71. Found: C, 62.57; H, 5.37; N, 2.93.

EXAMPLE 10

{R(+)-N-[(5,6-Dichloro-2-oxo-9a-propyl-2,3,9,9a-tetrahydro-1H-fluoren-7-yl)oxy]acetyl}-S(−)-tyrosine R(+)[(5,6-Dichloro-3-oxo-9a-propyl-2,3,9,9a-tetrahydro-1H-fluoren-7-yl)oxy]acetic acid (3.69 g., 10 mMole) and 1,1'-carbonyldiimidazole (1.95 g., 12 mMole) in dry tetrahydrofuran (100 mL) was stirred in an atmosphere of dry nitrogen at ambient temperature for 30 minutes. S(−)Tyrosine methyl ester (2.34 g., 12 mMole) was added and the mixture stirred at ambient temperature for 16 hours. The solvent was removed by distillation in vacuo and the residue dissolved in methylene chloride (75 mL), washed 3 times with water (50 mL portions) and dried over anhydrous magnesium sulfate. The solvent was removed by evaporation in vacuo and the residue treated with ethanol (25 mL) and 0.2 normal sodium hydroxide solution (75 mL). The mixture was stirred and refluxed for 10 minutes, whereby a clear solution formed. The mixture was cooled in ice and acidified with acetic acid. The solid that separated was removed by filtration, treated with water containing 1-methylpiperazine, filtered and the filtrate acidified with acetic acid. The precipitate that formed was removed by filtration, washed with water and dried. The yield was 5.31 g. The product was treated with water containing sodium bicarbonate and the resulting solution acidified with hydrochloric acid. The precipitate that formed was removed by filtration, washed with water and dried. The yield was 5.00 g., m.p. 137°–140° C.

Anal. Calc. for $C_{27}H_{27}ClNO_6$: C, 60.91; H, 5.11; N, 2.63%. Found: C, 60.83; H, 5.17; N, 2.87%.

EXAMPLE 11

{R(+)-N-[(5,6-Dichloro-3-oxo-9a-propyl-2,3,9,9a-tetrahydro-1H-fluoren-7-yl)oxy]acetyl}S(+)-histidine R(+)-[(5,6-Dichloro-3-oxo-9a-propyl2,3,9,9a-tetrahydro-1H-fluoren-7-yl)oxy]acetic acid (3.69 g., 10 mMole) and 1,1'-carbonyldiimidazole (1.95 g., 12 mMole) in dry tetrahydrofuran (125 mL) was stirred in an atmosphere of dry nitrogen at ambient temperature for 30 minutes. S(+)Histidine methyl ester dihydrochloride (2.91 g., 12 mMole) and triethylamine (2.42 g., 24 mMole) was added over the mixture stirred at ambient temperature for 16 hours. The solvent was removed by distillation in vacuo and the residue dissolved in methylene chloride (75 mL), washed 3 times with a mixture of brine and water (50 mL portions) and dried over anhydrous magnesium sulfate. The solvent was removed by evaporation in vacuo and the residue treated with ethanol (25 mL) and 0.2 normal sodium hydroxide solution (75 mL). The mixture was stirred and refluxed for 25 minutes, whereby a clear solution formed. The mixture was cooled in ice and acidified with hydrochloric acid. The semi-solid that formed was decanted full of water and then treated with acetonitrile whereby a yellow solid formed which was removed by filtration, washed with acetonitrile and dried to give 4.09 g. of product. The solid was dissolved in N,N-dimethylformamide (15 mL) by warming, filtered, cooled and treated with acetonitrile (65 mL). The precipitate that formed was removed bY filtration, washed with acetonitrile and dried to give 2.07 g. of pure product.

Anal. Calc. for $C_{24}H_{25}Cl_2N_3O_5 \cdot H_2O$: C, 54.96; H, 5.18; N, 8.01. Found: C, 54.90; H, 5.14; N, 8.04.

EXAMPLE 12

{R(+)-N-([5,6-Dichloro-9a-(2-hydroxy-ethyl)-3-oxo-2,3,9,9a-tetrahydro-1H-fluoren-7-yl]-oxy}acetyl)-S(-)-proline By carrying out a reaction as described in Example 7, except that the R(+)[(5,6-dichloro-3-oxo-9a-propyl-2,3,9,9a-tetrahydro-1H-fluoren-7-yl)oxy]acetic acid is replaced by an equimolar quantity of R(+)-[(5,6-dichloro-9a-(2-hydroxyethyl)-3-oxo-2,3,9,9a-tetrahydro-1H-fluoren-6-yl]oxy)-acetic acid and the S(+)-serine methyl ester hydrochloride is replaced by an equimolar quantity of S(−) proline methyl ester hydrochloride. There is obtained {R(+)-N-{[5,6-dichloro-9a-(2-hydroxyethyl)-3-oxo-2,3,9,9a-tetrahydro-1H-fluoren-7-yl]oxy}acetyl}-S(−)-proline.

Other amides derived from natural amino acids can be made by the methods described in Examples 7 through 12 by using the appropriate [(5,6-dichloro-3-oxo-9a-substituted-2,3,9,9a-tetrahydro-1H-fluoren-7yl)oxy]acetic acid and natural amino acid ester or salt thereof.

EXAMPLE 13

Parenteral solution of the sodium salt of R(+)-N-cyano-[5,6-dichloro-3-oxo-9a-propyl-2,3,9,9a-tetrahydro-1H-fluoren-7-yl)oxy]acetamide The R(+)-N-cyano-[5,6-dichloro-3-oxo-9a-propyl-2,3,9,9a-propyl-2,3,9,9a-tetrahydro-1H-fluoren-7-yl)oxy]acetamide (Example 5) (500 mg) is dissolved by stirring and warming with a solution of 0.25N sodium bicarbonate (5.2 mL). The solution is diluted to 10 mL with water and sterilized by filtration. All the water that is used in the preparation is pyrogen-free. The concentration of the active ingredient (calculated as free acid) in the final solution is 5%.

EXAMPLE 14

Parenteral solution of the sodium salt of R(+)-N-(5-tetrazolyl)-[(5,6-dichloro-3-oxo-9a-propyl-2,3,9,9a-tetrahydro-1H-fluoren-7-yl)oxy]acetamide The R(+)-N-(2-tetrazolyl)-[(5,6-dichloro-3-oxo-9a-propyl-2,3,9,9a-tetrahydro-1H-fluoren-7-yl)oxy]acetamide (Example 6) (500 mg) is dissolved by stirring and warming with a solution of 0.25N sodium bicarbonate (4.7 mL). The solution is diluted to 10 mL with water and sterilized by filtration. All the water that is used in the preparation is pyrogen-free. The concentration of the active ingredient (calculated as free acid) in the final solution is 5%.

EXAMPLE 15

Parenteral solution of the sodium salt of R(+)-N-ethanesulfonyl-[5,6-dichloro-3-oxo-9a-propyl-2,3,9,9a-tetrahydro-1H-fluoren-7-yl)oxy]acetamide The R(+)-N-ethanesulfonyl-[5,6-dichloro-3-oxo-9a-propyl-2,3,9,9a-tetrahydro-1H-fluoren-7-yl)oxy]acetamide (Example 2) (500 mg) is dissolved by stirring and warming with a solution of 0.25N sodium bicarbonate (4.4 mL). The solution is diluted to 10 mL with water and sterilized by filtration. All the water that is used in the preparation is pyrogen-free. The concentration of the active ingredient (calculated as free acid) in the final solution is 5%.

EXAMPLE 16

Parenteral solution of the sodium salt of {R(+)-N-[(5,6-dichloro-3-oxo-9a-propyl-2,3,9,9a-tetrahydro-1H-7-yl)oxy]acetyl1-S(+)-serine The {R(+)-N-[(5,6-dichloro-3-oxo-9a-propyl-2,3,9,9a-tetrahydro-1H-fluoren-7-yl)oxy]acetyl}S(+)-serine (Example 7) (500 mg) is dissolved by stirring and warming with a solution of 0.25N sodium bicarbonate (4.5 mL). The solution is diluted to 10 mL with water and sterilized by filtration. All the water that is used in the preparation is pyrogen-free. The concentration of the active ingredient (calculated as free acid) in the final solution is 5%.

EXAMPLE 17

Parenteral solution of the sodium salt of {R(+)-N-[5,6-dichloro-3-oxo-9a-propyl-2,3,9,9a-tetrahydro-1H-fluoren-7-yl)oxy]acetyl}-S(+)-leucine The {R(+)-N-[5,6-dichloro-3-oxo-9a-propyl-2,3,9,9a-tetrahydro-1H-fluoren-7-yl)oxy]acetyl}S(+)-leucine (Example 8) (500 mg) is dissolved by stirring and warming with a solution of 0.25N sodium bicarbonate (4.3 mL). The solution is diluted to 10 mL with water and sterilized by filtration. All the water that is used in the preparation is pyrogen-free. The concentration of the active ingredient (calculated as free acid) in the final solution is 5%.

EXAMPLE 18

Parenteral solution of the sodium salt of {R(+)-N-[(5,6-dichloro-3-oxo-9a-propyl-2,3,9,9a-tetrahydro-1H-fluoren-7-yl)oxy]acetyl)-S(−)phenylalanine The {R(+)-N-[(5,6-dichloro-3-oxo-9a-propyl-2,3,9,9a-tetrahydro-1H-fluoren-7-yl)oxy]acetyl}-S(−) phenylalanine (Example 9) (500 mg) is dissolved by stirring and warming with a solution of 0.25N sodium bicarbonate (4.0 mL). The solution is diluted to 10 mL with water and sterilized by filtration. All the water that is used in the preparation is pyrogen-free. The concentration of the active ingredient (calculated as free acid) in the final solution is 5%.

EXAMPLE 19

Dry-Filled Capsules Containing 100 mg of Active Ingredient (free base) Per Capsule

|  | Per Capsule |
| --- | --- |
| R(+)—N—methanesulfonyl-[(5,6-dichloro-3-oxo-9a-propyl-2,3,9,9a-tetrahydro-1H—fluoren-7-yl)oxy]acetamide | 100 mg |
| Lactose | 99 mg |
| Magnesium Stearate | 1 mg |
| Capsule (Size No. 1) | 200 mg |

The R(+)-N methanesulfonyl-[(5,6-dichloro-3-oxo-9a-propyl-2,3,9,9a-tetrahydro-1H-fluoren-7-yl)-oxy]acetamide (Example 4) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 20

Dry-Filled Capsules Containing 100 mg of Active Ingredient (free base) Per Capsule

|  | Per Capsule |
|---|---|
| {R(+)—N—[(5,6-Dichloro-3-oxo-9a-propyl-2,3,9,9a-tetrahydro-1H—fluoren-7-yl)-oxy]acetyl}-S(—)-tyrosine | 100 mg |
| Lactose | 99 mg |
| Magnesium Stearate | 1 mg |
| Capsule (Size No. 1) | 200 mg |

The {R(+)-N-[(5,6-dichloro-3-oxo-9a-propyl-2,3,9,9a-tetrahydro-1H-fluoren-7-yl)-oxy]acetyl}-S(—)-tyrosine (Example 10) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 21

Dry-Filled Capsules Containing 100 mg of Active Ingredient (free base) Per Capsule

|  | Per Capsule |
|---|---|
| {R(+)—N—[(5,6-Dichloro-3-oxo-9a-propyl-2,3,9,9a-tetrahydro-1H—fluoren-7-yl)-oxy]acetyl}-S(+)-histidine | 100 mg |
| Lactose | 99 mg |
| Magnesium Stearate | 1 mg |
| Capsule (Size No. 1) | 200 mg |

The {R(+)-N-[(5,6-dichloro-3-oxo-9a-propyl-2,3,9,9a-tetrahydro-1H-fluoren-7-yl)-oxy]acetyl}S(+)-histidine (Example 11) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 22

Dry-Filled Capsules Containing 100 mg of Active Ingredient (free base) Per Capsule

|  | Per Capsule |
|---|---|
| {R(+)—N—[(5,6-Dichloro-9a-(2-hydroxyethyl)-3-oxo-2,3,9,9a-tetrahydro-1H—fluoren-7-yl)-oxy]-acetyl}-S(—)-proline | 100 mg |
| Lactose | 99 mg |
| Magnesium Stearate | 1 mg |
| Capsule (Size No. 1) | 200 mg |

The {R(+)-N-[(5,6-dichloro-9a-(2-hydroxyethyl)-3-oxo-2,3,9,9a-tetrahydro-1H-fluoren-7-yl)-oxy]acetyl}-S(—)-proliner (Example 12) is reduced to a No. 60 powder and then the lactose and magnesium stearate are passed through a No. 60 bolting cloth onto the powder and the combined ingredients admixed for 10 minutes and then filled into a No. 1 dry gelatin capsule.

What is claimed is:

1. A compound of the formula:

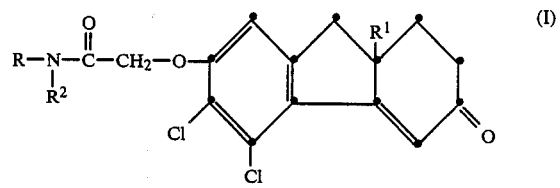

wherein:

R is —CN, SO$_2$—C$_1$—C$_6$ alkyl,

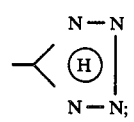

R$^1$ is lower alkyl, branched or unbranched, containing from 1 to 3 carbon atoms or hydroxy-lower alkyl containing 1 to 3 carbon atoms;

R$^2$ is H.

2. A compound of the formula:

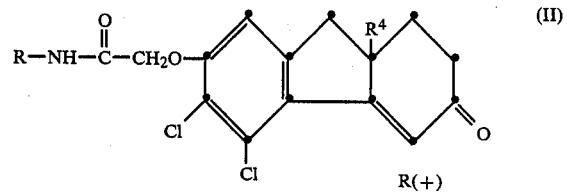

wherein:

R is —CN, SO$_2$—C$_1$—C$_6$ alkyl,

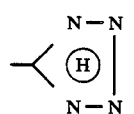

R$^4$ is propyl or 2-hydroxyethyl

3. A compound according to claim 2, which is R(+)-N-ethanesulfonyl-[5,6-dichloro-3-oxo-9a-propyl-2,3,9,9a-tetrahydro-1H-fluoren-7-yl)oxy]acetamide.

4. A compound of claim 2, which is R(+)-N-methanesulfonyl-[5,6-dichloro-3-oxo-9a-propyl-2,3,9,9a-tetrahydro-1H-fluoren-7-yl)oxy]acetamide.

5. A compound of claim 2, which is R(+)-N-cyano-[5,6-dichloro-3-oxo-9a-propyl-2,3,9,9a-tetrahydro-1H-fluoren 7-yl)oxy]acetamide.

6. A compound of claim 2, which is R(+)-5-tetrazolyl)-[5,6-dichloro-3-oxo-9a-propyl-2,3,9,9a-tetrahydro-1H-fluoren-7-yl)oxy]acetamide.

7. A pharmaceutical composition comprising a pharmaceutical carrier and an effective amount of a compound of claim 1.

* * * * *